United States Patent [19]
Noelle et al.

[11] Patent Number: 5,833,987
[45] Date of Patent: Nov. 10, 1998

[54] TREATMENT OF T CELL MEDIATED AUTOIMMUNE DISORDERS

[75] Inventors: Randolph J. Noelle, Cornish, N.H.; Eric Claassen, Pijnacker, Netherlands

[73] Assignees: Trustees of Dartmouth College, Hanover, N.H.; Nederlanse Organisatie Voor Teogepastnatuurwetenschappelijk Onderzoek TNO, Rijswijk, Netherlands

[21] Appl. No.: 481,735

[22] Filed: Jun. 7, 1995

[51] Int. Cl.⁶ .................................... A61K 39/395
[52] U.S. Cl. ..................... 424/154.1; 424/130.1; 424/133.1; 424/141.1; 424/142.1; 424/143.1; 424/144.1; 424/153.4; 424/173.1
[58] Field of Search ............... 424/133.1, 141.1, 424/142.1, 144.1, 154.1, 130.1, 173.1

[56] References Cited

PUBLICATIONS

Franco et al. (Apr. 1994) Eur. J. Immunol. vol. 24(4) 940–946.
Durie et al. (1993) Science vol. 261 (5126):1328–30.
Mohan et al. (Apr. 24–28, 1994) FASEB Journal vol. 8 (4–5):A967.
Durie et al. (Oct. 1994) Clinical Immunopathol. vol. 73(1): 11–18.
Laman et al. (Oct. 23–27, 1994) Journal of Neuroimmunology vol. 54 (1–2):175.
Harris et al. (1993) Tibtech vol. 11:42–44.
Queen et al. (1989) Proc. Natl. Acad. Sci. vol. 86:10029–33.

*Primary Examiner*—Lila Feisee
*Assistant Examiner*—Phillip Gambel
*Attorney, Agent, or Firm*—Burns, Doane, Swecker & Mathis, LLP

[57] ABSTRACT

Method for the treatment of multiple sclerosis and other T cell mediated autoimmune disorders is described. The method involves administering to a subject a therapeutically effective amount of an antagonist of a receptor on a surface of a T cell which mediates contact dependent helper effector functions, for example, an anti-gp39 antibody.

2 Claims, 4 Drawing Sheets

Days of MR1 Treatment

TREATMENT OF T CELL MEDIATED AUTOIMMUNE DISORDERS

GOVERNMENT FUNDING

The work leading to this invention was supported by one or more grants from the U.S. government. The government may have rights in the invention.

BACKGROUND OF THE INVENTION

Autoimmune diseases are characterized by attack of the immune system of an individual against its own tissues. Autoimmune diseases usually result from breakdown of tolerance of the immune system to its own antigens. The specific antigens recognized by the immune system in the various autoimmune diseases can be present systematically or they can be organ specific. For example, systemic lupus erthematosus (SLE) is characterized by the presence of autoantibodies to DNA, ribonucleoproteins, histones, and other molecules that are not organ specific. Other autoimmune diseases are characterized by the destruction of mostly one organ. Such autoimmune diseases include type I diabetes, in which the insulin producing β cells of the islets of Langerhans in the pancreas are destroyed.

In some autoimmune diseases, tissue destruction occurs primarily as a result of the production of high levels of autoantibodies. Such diseases include rheumatoid arthritis, characterized by destruction of the joint cartilage and inflammation of the synovium. Patients with rheumatoid arthritis have an accumulation of immune complexes in their joints which are formed by association of autoantibodies against the Fc portion of IgG and IgG molecules. These immune complexes activate the complement cascade which results in tissue damage. Myasthenia gravis, a disease of progressive muscle weakness, is caused by the production of autoantibodies reactive to acetylcholine receptors in the motor end plates of neuromuscular junctions.

In other autoimmune diseases, tissue destruction does not appear to be primarily mediated by production of autoantibodies, but rather by auto-reactive T lymphocytes. For example, experimental allergic encephalomyelitis (EAE), an animal model for multiple sclerosis, and characterized by demyelination in the brain and the spinal cord, can be induced in naive animals by transfer of CD4+T cells from diseased animals. Thus, it is generally considered that EAE represents a T cell mediated autoimmune disease, rather than a B cell mediated autoimmune disease (Ben-Nun, A. et al. (1981) *Eur. J. Immunol.* 11, 195).

Multiple sclerosis (MS) is a common demyelinating disease of the brain and spinal cord. It is a progressive disease that is characterized by remissions and exacerbations of neurologic dysfunction affecting different regions of the central nervous system. The symptoms of the disease result from a focus of inflammatory demyelination, which later forms a scar, appearing as a "plaque" in the white matter of the brain, brain stem or spinal cord. Presently, there is no definitive diagnostic test available for MS and diagnoses and treatment regimes are being formulated based on such factors as the extent of a patient's symptoms and/or the age of the patient at the time of onset of the exacerbations of neurologic dysfunction.

Patients having MS typically have been treated with steroids with a goal of either sending the patient into remission or slowing the progression of the disease in the patient. Other drugs have been used to treat particular symptoms of the disease, e.g. muscle relaxants. Recent developments in treatments available for MS include the administration of beta-interferon. Beta interferon has shown some promise for slowing the progression of the disease. However, effective treatments for MS are still needed.

SUMMARY OF THE INVENTION

This invention pertains to methods for treating (therapeutically or prophylactically) a T cell mediated autoimmune disorder, such as multiple sclerosis. The method comprises administering to the subject a therapeutically or prophylactically effective amount of an antagonist of a receptor on a surface of a T cell which mediates contact dependent helper effector functions. In a preferred embodiment the antagonist administered is an antibody or fragment thereof which specifically binds to the T cell receptor gp39.

DETAILED DESCRIPTION OF THE INVENTION

Figure 1A:
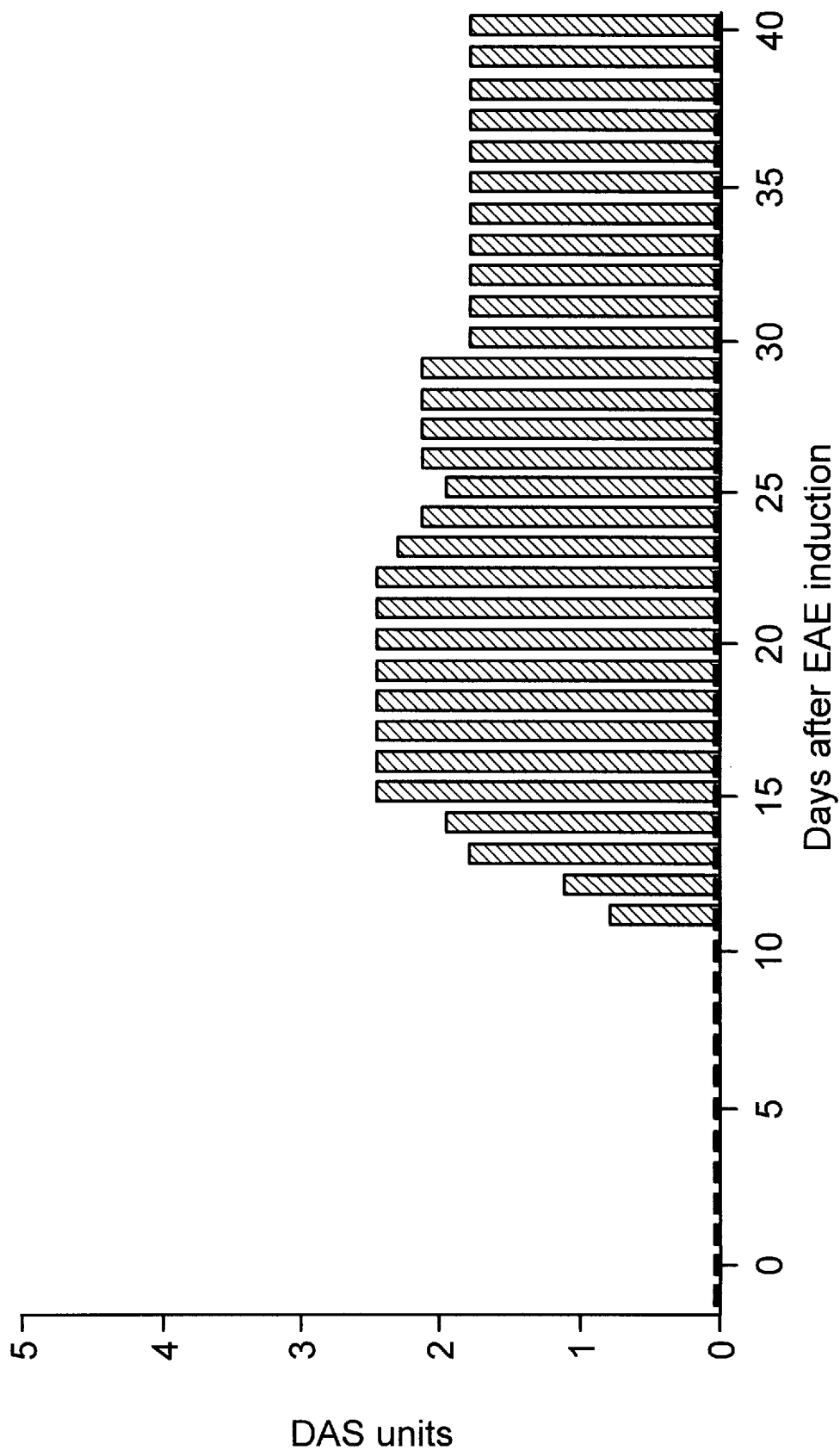
FIG. 1 is a graphical representation of DAS units measured daily in mice injected at day 0 with 75 µg (Panel A) or 300 µg (Panel B) of PLP-peptide with an anti-gp39 antibody (black bars) or with PBS (grey bars) showing that anti-gp39 administration prevents the development of experimental allergic encephalomyelitis EAE.

This invention pertains to the treatment of T cell mediated autoimmune disorder such as multiple sclerosis. The disease is treated by administering an antagonist to a receptor on the surface of T cells which mediates contact dependent T cell helper effector function.

As defined herein, a "molecule or receptor which mediates contact dependent helper effector functions" is one which is expressed on a Th cell and interacts with a ligand on an effector cell (e.g., a B cell), wherein the interaction of the receptor with its ligand is necessary for generation of an effector cell response (e.g., B cell activation). In addition to being involved in effector cell responses, it has been found that such a molecule is involved in the response of the T cell to antigen.

In a preferred embodiment, the receptor on the surface of the T cell which mediates contact-dependent helper effector functions is gp39. In this embodiment, the antagonist is a molecule which inhibits the interaction of gp39 with its ligand on a cell which presents antigen to the T cell. A particularly preferred gp39 antagonist is an anti-gp39 antibody. Alternatively, the gp39 antagonist is a soluble form of a gp39 ligand, for example soluble CD40.

The method of the invention is based at least in part on the observation that administration of anti-gp39 antibodies to mice prevents induction of EAE and reverses the disease in animals having EAE. Thus, it has been found that an agent which inhibits the interaction of gp39 on a T cell with its ligands(s) on other cells is effective, both prophylactically and therapeutically, in treating a typical T cell mediated autoimmune disease. This result is surprising in view of previous studies which have attributed to gp39 a primary role in regulating B cell responses. The finding that anti-gp39 antibodies are effective in treating T cell mediated autoimmune disease forms the basis of the present invention. According to the invention, subjects having a T cell mediated autoimmune disease, such as multiple sclerosis, are treated by administration of agents that mimic the effect of anti-gp39 antibodies.

T CELL MEDIATED AUTOIMMUNE DISEASES

The language "autoimmune disorder" is intended to include disorders in which the immune system of a subject reacts to autoantigens, such that significant tissue or cell destruction occurs in the subject. The term "autoantigen" is intended to include any antigen of a subject that is recognized by the immune system of the subject. The terms "autoantigen" and "self-antigen" are used interchangeably herein. The term "self" as used herein is intended to mean any component of a subject and includes molecules, cells, and organs. Autoantigens may be peptides, nucleic acids, or other biological substances. The language "T cell mediated autoimmune disorder" is intended to include autoimmune disorders in which the reaction to self primarily involves cell-mediated immune mechanisms, as opposed to humoral immune mechanisms. Thus, the methods of the invention pertain to treatments of autoimmune disorders in which tissue destruction is primarily mediated through activated T cells and immune cells other than B lymphocytes. However, even though the methods of the invention are intended for treatment of autoimmune disorders in which reaction to self is primarily mediated by cells other than B cells, the autoimmune disorders may be characterized by the presence of autoantibodies. For example, EAE, a T cell mediated autoimmune disorder, which can be treated by a method of the invention, is frequently associated with the presence of autoantibodies to components of the central nervous system, such as myelin basic protein. Non limiting examples of T cell mediated autoimmune disorders that can be treated by the methods of the invention include multiple sclerosis, EAE, diabetes type I, oophoritis, and thyroiditis.

gp39 ANTAGONISTS

According to the methods of the invention, a gp39 antagonist is administered to a subject to interfere with the interaction of gp39 on T cells with a gp39 ligand on antigen presenting cells, such as B cells and thereby to prevent, alleviate or ameliorate the disorder. A gp39 antagonist is defined as a molecule which interferes with this interaction. As described more fully below, the gp39 antagonist can be an antibody directed against gp39 (e.g., a monoclonal antibody against gp39), a fragment or derivative of an antibody directed against gp39 (e.g., Fab or F(ab)'2 fragments, chimeric antibodies or humanized antibodies), soluble forms of a gp39 ligand (e.g., soluble CD40), soluble forms of a fusion protein of a gp39 ligand (e.g., soluble CD40Ig), or pharmaceutical agents which disrupt or interfere with the gp39-CD40 interaction.

A. Antibodies

To prepare anti-gp39 antibodies, a mammal (e.g., a mouse, hamster, or rabbit) can be immunized with an immunogenic form of gp39 protein or protein fragment (e.g., peptide fragment) which elicits an antibody response in the mammal. A cell which expresses gp39 on its surface can also be used as the immunogen. Alternative immunogens include purified gp39 protein or protein fragments. gp39 can be purified from a gp39-expressing cell by standard purification techniques, e.g., gp39 cDNA (Armitage et al., *Nature*, 357:80–82 (1992); Lederman et al.,*J. Exp. Med.*, 175:1091–1101 (1992); Hollenbaugh et al., *EMBO J.*, 11:4313–4319 (1992)) can be expressed in a host cell, e.g., bacteria or a mammalian cell line, and gp39 protein purified from the cell culture by standard techniques. gp39 peptides can be synthesized based upon the amino acid sequence of gp39 (disclosed in Armitage et al., *Nature*, 357:80–82 (1992); Lederman et al., *J. Exp. Med.*, 175:1091–1101 (1992); Hollenbaugh et al.,*EMBO J.*, 11:4313–4319 (1992)) using known techniques (e.g. F-moc or T-boc chemical synthesis). Techniques for conferring immunogenicity on a protein include conjugation to carriers or other techniques well known in the art. For example, the protein can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) (Allen R. Bliss, Inc., pages 77–96), and screening of combinatorial antibody libraries (Huse et al., *Science* (1989) 246:1275). Hybridoma cells can be screened immunochemically for production of antibodies specifically reactive with the protein or peptide and monoclonal antibodies isolated.

The term antibody as used herein is intended to include fragments thereof which are specifically reactive with a gp39 protein or peptide thereof or gp39 fusion protein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-gp39 portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes gp39. See, for example, Morrison et al., *Proc. Natl. Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes the monoclonal or chimeric antibodies specifically reactive with a gp39 protein or peptide can be further humanized by producing human variable region chimeras, in which parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., *Proc. Natl. Acad. Sci. U.S.A.*, 80:7308–7312 (1983); Kozbor et al., *Immunology Today*, 4:7279 (1983); Olsson et al., *Meth. Enzymol.*, 92:3–16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

Another method of generating specific antibodies, or antibody fragments, reactive against a gp39 protein or peptide is to screen expression libraries encoding immunoglobulin genes, or portions thereof, expressed in bacteria with a gp39 protein or peptide. For example, complete Fab fragments, VH regions and FV regions can be expressed in bacteria using phage expression libraries. See for example Ward et al., *Nature*, 341:544–546: (1989); Huse et al., *Science*, 246:1275–1281 (1989); and McCafferty et al., *Nature*, 348:552–554 (1990). Screening such libraries with, for example, a gp39 peptide can identify immunoglobulin fragments reactive with gp39. Alternatively, the SCID-hu mouse (available from Genpharm) can be used to produce antibodies, or fragments thereof.

Methodologies for producing monoclonal antibodies directed against gp39, including human gp39 and mouse gp39, and suitable monoclonal antibodies for use in the methods of the invention, are described in PCT Patent Application No. WO 95/06666 entitled "Anti-gp39 Antibodies and Uses Therefor", the teachings of which are incorporated by reference. Particularly preferred anti-human gp39 antibodies of the invention are mAbs 24-31 and 89-76, produced respectively by hybridomas 24-31 and 89-76. The 89-76 and 24–31 hybridomas, producing the 89-76 and 24-31 antibodies, respectively, were deposited under the provisions of the Budapest Treaty with the American Type Culture Collection, Parklawn Drive, Rockville, Md., on Sep. 2, 1994. The 89-76 hybridoma was assigned ATCC Accession Number HB11713 and the 24-31 hybridoma was assigned ATCC Accession Number HB11712.

Recombinant anti-gp39 antibodies, such as chimeric and humanized antibodies, can be produced by manipulating nucleic acid (e.g., DNA) encoding an anti-gp39 antibody according to standard recombinant DNA techniques. Accordingly, another aspect of this invention pertains to isolated nucleic acid molecules encoding immunoglobulin heavy or light chains, or portions thereof, reactive with gp39, particularly human gp39. The immunoglobulin-encoding nucleic acid can encode an immunoglobulin light or heavy chain variable region, with or without a linked heavy or light chain constant region (or portion thereof).

Such nucleic acid can be isolated from a cell (e.g., hybridoma) producing an anti-human gp39 mAb by standard techniques. For example, nucleic acid encoding the 24-31 or 89-76 mAb can be isolated from the 24-31 or 89-76 hybridoma, respectively, by cDNA library screening, PCR amplification or other standard technique. Following isolation of, and possible further manipulation of, Moreover, nucleic acid encoding an anti-human gp39 mAb can be incorporated into an expression vector and introduced into a host cell to facilitate expression and production of recombinant forms of anti-human gp39 antibodies.

B. Soluble Ligands for gp39

Other gp39 antagonists which can be used to induce T cell tolerance are soluble forms of a gp39 ligand. A monovalent soluble ligand of gp39, such as soluble CD40 can bind gp39, thereby inhibiting the interaction of gp39 with CD40 on B cells. The term "soluble" indicates that the ligand is not permanently associated with a cell membrane. A soluble gp39 ligand can be prepared by chemical synthesis, or, preferably by recombinant DNA techniques, for example by expressing only the extracellular domain (absent the transmembrane and cytoplasmic domains) of the ligand. A preferred soluble gp39 ligand is soluble CD40. Alternatively, a soluble gp39 ligand can be in the form of a fusion protein. Such a fusion protein comprises at least a portion of the gp39 ligand attached to a second molecule. For example, CD40 can be expressed as a fusion protein with immunoglobulin (i.e., a CD40Ig fusion protein). In one embodiment, a fusion protein is produced comprising amino acid residues of an extracellular domain portion of the CD40 molecule joined to amino acid residues of a sequence corresponding to the hinge, CH2 and CH3 regions of an immunoglobulin heavy chain, e.g., Cγl, to form a CD40Ig fusion protein (see e.g., Linsley et al. (1991) *J. Exp. Med.* 1783:721–730; Capon et al. (1989) *Nature* 337, 525–531; and Capon U.S. Pat. No. 5,116,964). The fusion protein can be produced by chemical synthesis, or, preferably by recombinant DNA techniques based on the cDNA of CD40 (Stamenkovic et al., *EMBO J.*, 8:1403–1410 (1989)).

An antagonist of the invention is administered to subjects in a biologically compatible form suitable for pharmaceutical administration in vivo. By "biologically compatible form suitable for administration in vivo" is meant a form of the antagonist to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. A gp39 antagonist can be administered in any pharmacological form, optionally in a pharmaceutically acceptable carrier. Administration of a therapeutically active amount of the antagonist is defined as an amount effective, at dosages and for periods of time necessay to achieve the desired result. For example, a therapeutically active amount of an antagonist of gp39 may vary according to factors such as the disease state, age, sex, and weight of the individual, and the ability of the antagonist to elicit a desired response in the individual. Dosage regima may be adjusted to provide the optimum therapeutic response. For example, several divided doses may be administered daily or the dose may be proportionally reduced as indicated by the exigencies of the therapeutic situation.

The active compound (e.g., antagonist) may be administered in a convenient manner such as by injection (subcutaneous, intravenous, etc.), oral administration, inhalation, transdermal application, or rectal administration.

Depending on the route of administration, the active compound may be coated in a material to protect the compound from the action of enzymes, acids and other natural conditions which may inactivate the compound. A preferred route of administration is by intravenous injection.

To administer an antagonist of gp39 by other than parenteral administration, it may be necessary to coat the antagonist with, or co-administer the antagonist with, a material to prevent its inactivation. For example, an antagonist can be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., an antagonist of gp39) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antagonist) plus any additional desired ingredient from a previously sterile-filtered solution thereof.

When the active compound is suitably protected, as described above, the protein may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

This invention is further illustrated by the following examples which should not be construed as limiting. The contents of all references, patents and published patent applications cited throughout this application are hereby incorporated by reference.

EXAMPLE 1

EAE prevention by anti-gp39 antibody administration

This example demonstrates that administration of anti-gp39 antibodies to mice prevents induction of experimental allergic encephalomyelitis (EAE), an animal model for multiple sclerosis.

EAE is a well characterized model of a T cell mediated autoimmune disease and is an instructive model for the human autoimmune disease multiple sclerosis. EAE can be induced in susceptible animals, such as mice, by immunizing the animals with myelin basic protein (MBP), proteolipid protein (PLP), myelin oliogodendrocyte protein (MOG), or synthetic peptides based on the sequences of these myelin associated proteins together with an adjuvant containing pertussis bacteria. One to two weeks after immunization, the animals develop encephalomyelitis, characterized by perivascular infiltrates containing lymphocytes and macrophages and the development of demyelination in the brain and the spinal cord. The animals show acute, chronic or chronic relapsing paralysis. In this example, the effect of administration of anti-gp39 antibodies on development of EAE in susceptible mice was analyzed.

EAE was induced in susceptible mice by subcutaneous injections (day 0) of an emulsion containing 70 µg or 300 µg PLP-peptide in 50 µl PBS and 25 µg Mycobacteria tuberculosis (H37RA, Difco) in 50 µl of complete Freuds adjuvant at two sites in the abdominal flanks of the mice. 200 µl Bordetella pertussis suspension ($10.10^{10}$ in 1 ml PBS) was given intravenously at the same time as the peptide and two days later. The PLP-peptide injected in the mice has an amino acid sequence corresponding to amino acid residues 139 to 151 of rat PLP (Dautigny et al., *FEBS Lett.* 188:33, 1985). PLP-peptide was synthesized with f-moc protected aminoacids according to the solid phase synthesis method (Merrifield, *J. Am. Chem. Soc.* 85:2149, 1963). Immunization with this peptide results in the development of acute EAE, which is clinically and pathologically identical to that induced by sensitization with whole central nervous system (CNS) myelin or with MBP (Tuohy et al., *J. Immunol.* 142:1523, 1989; Sobel et al., *J. Neuropathol. Exp. Neurol.* 49:468, 1990).

To determine the effect of anti-gp39 on the course of the disease, mice were injected on day 0 with PLP-peptide, as described above, and further injected intraperitoneally with 125 μg hamster anti-gp39 Mabs (Noelle et al., *Proc. Natl. Acad. Sci. USA* 89:6550, 1992) in 200 μl PBS or with 125 μg normal hamster antibodies (Serva Feinbiochemica) in 200 μl PBS (control animals) on days 0, 2, and 4. The severity of EAE clinical signs was evaluated each day and graded according to average disability scale (DAS) scores: grade 0=no clinical signs, grade 1=tail weakness, grade 2=mild paraparesis and ataxia of the hind legs, grade 3=severe paraparesis or ataxia of the hind legs, grade 4=moribund, grade 5=dead due to EAE.

Figure 1B:
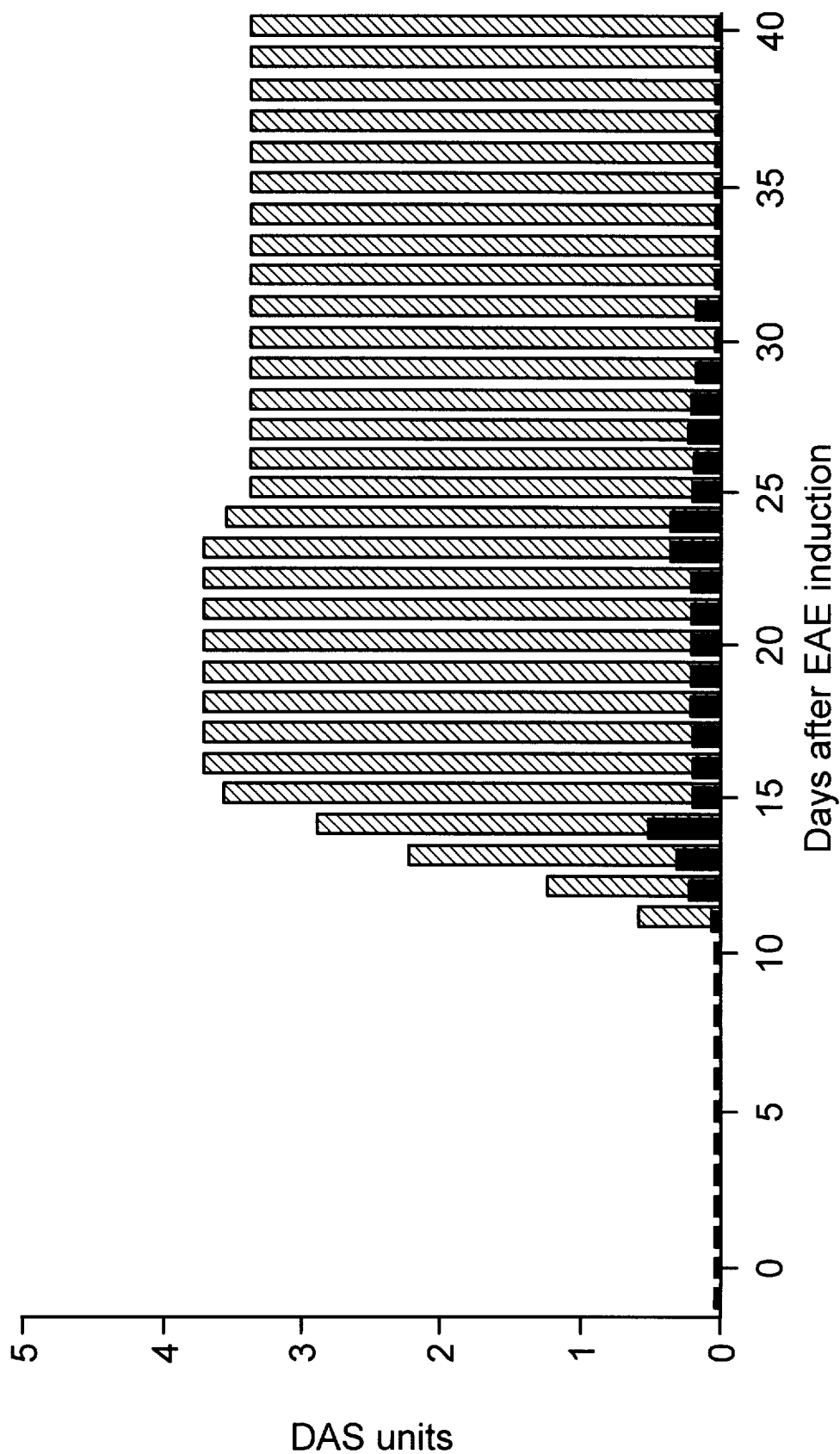

FIG. 1 represents the course of the disease in mice injected with 70 μg of PLP-peptide (Panel A) or with 300 μg of PLP-peptide (Panel B) and treated with anti-gp39 or control antibody. DAS scores, which reflect the severity of the disease, of control mice and anti-gp39 treated mice are depicted in grey and black bars respectively.

The results indicate that animals having received the control antibody developed EAE, whereas animals having received anti-gp39 antibody were protected from induction of the disease. For animals having received control antibody, the first clinical signs of EAE became apparent on day eleven. In these animals, the highest DAS score was 2.33, which was observed on days 15–22 in animals injected with 75 μg of PLP-peptide (FIG. 1, Panel A, grey bars) and 3.6, observed on days 16–23 in animals injected with 300 μg PLP-peptide (FIG. 1, Panel B, grey bars). In contrast, animals which received the anti-gp39 monoclonal antibodies showed no clinical signs after induction of EAE with 75 μg of PLP-peptide (FIG. 1, Panel A, black bars) and only minor clinical signs, which completely disappeared at day 31, after induction of the disease with 300 μg of PLP-peptide (FIG. 1, Panel B, black bars).

Thus, administration of anti-gp39 antibodies to mice completely inhibited induction of EAE in these mice.

Induction of EAE by adoptive transfer of myelin reactive T-cells isolated from animals immunized with myelin components or obtained after in vitro activation with myelin components indicates that especially activated T-cells are responsible for the development of clinical characteristics after the inductive phase (Pettinelli and McFarlin, *J. Immunol.* 127:1420, 1979; Mokhtarion et al., *Nature* 309:356, 1984; Veen et al., *J. Neuroimmunol.* 21:183, 1989). However, the experiments described herein show that administration of anti-gp39 monoclonal antibodies prevents the development of EAE. In control groups, significant anti-PLP-peptide antibody responses were observed on day 14 (absorbance 1.92) and 21 (absorbance 2.15) in animals in which EAE was induced with low and high PLP-peptide dose, respectively. In contrast, significant anti-PLP-peptide antibody responses in the gp39 treated animals were observed first on day 14, and reached plateau levels on day 31 (absorbance 0.928) and 40 (absorbance 1.54) in animals which were injected with low and high PLP-peptide dose, respectively. The generation of significant anti-PLP-peptide antibody responses in anti-gp39 monoclonal antibodies treated mice, was postponed until day 14, which indicates that the anti-gp39 monoclonal antibodies had some effect on antibody production.

Thus, this example demonstrates that anti-gp39 prevent development of EAE and indicate that anti-gp39 antibodies can be used for treating T cell mediated autoimmune diseases, such as multiple sclerosis.

EXAMPLE 2

Reversal of EAE by anti-gp39 antibody administration

Example 1 showed the inhibitory effect of anti-gp39 antibody on induction of EAE. Thus, it was demonstrated that immunization of the mice at the time of induction of the disease prevented development of the disease. This example shows that administration of the antibody after induction of the disease leads to regression of the disease.

In this example, EAE was induced in female SJL/j mice (10–12 weeks old) by injection of an emulsion containing 150 μg PLP-peptide prepared as described above. For determining the effect of the anti-gp39 antibodies when administered to the mice after induction of the disease, mice were injected intraperitoneally with 125 μg anti-gp39 monoclonal antibodies (Noelle et al., *Proc. Natl. Acad. Sci. USA* 89:6550, 1992) in 200 μl of PBS (anti-gp39 treated mice) or with 200 μl PBS alone (control mice) on days 0, 2 and 4, on days 4, 6 and 8, or on days 7, 9 and 11. The results are presented as percentage suppression, and are a comparison of the total of daily DAS scores (from day 12 to 28) in anti-gp39 treated animals and in control animals.

Figure 2:
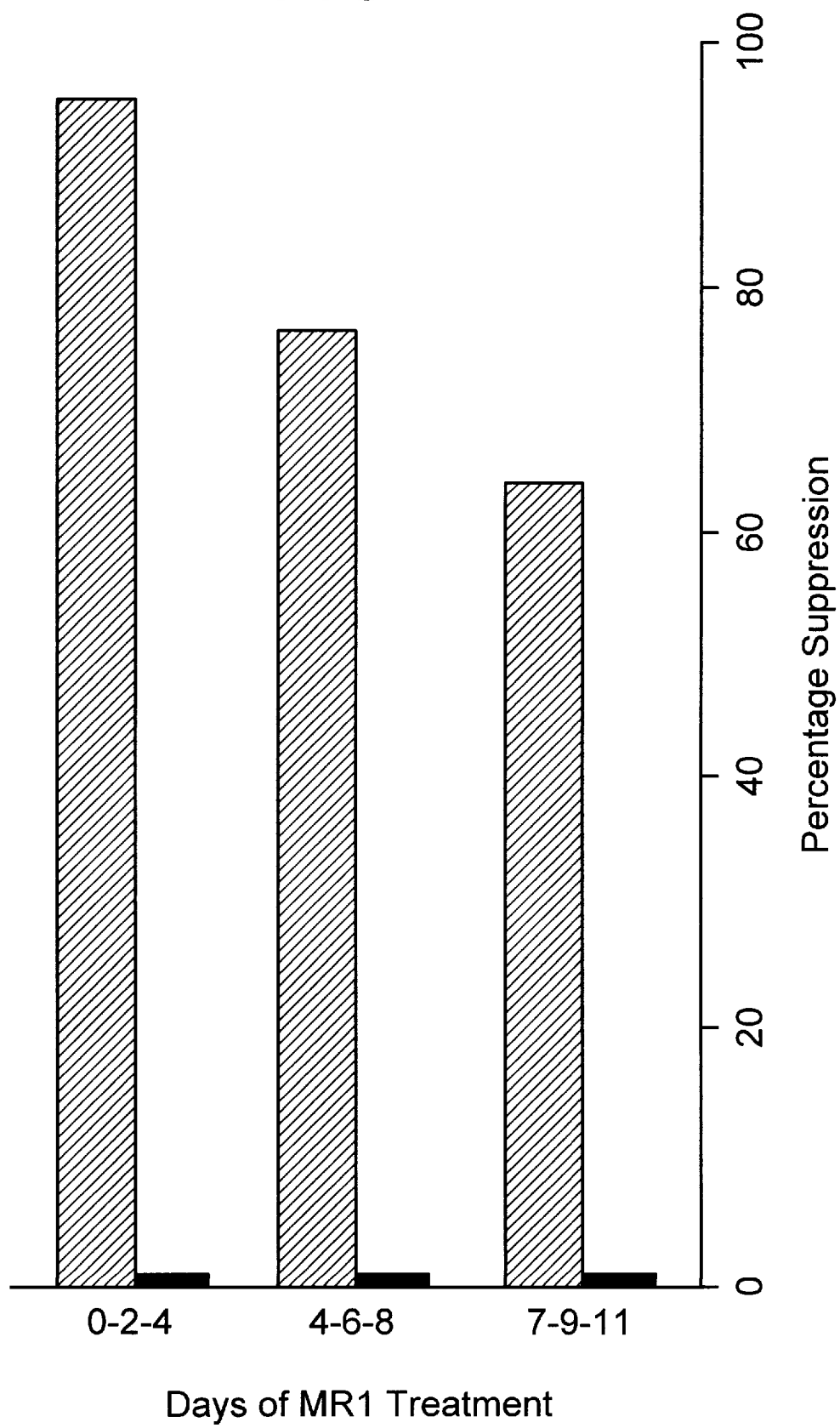
FIG. 2 is a graphical representation of the percentage suppression of EAE induction in mice injected with PLP-peptide at day 0 and further injected with anti-gp39 antibodies (black bars) or PBS (grey bars) at days 0, 2, and 6, or at days 4, 6, and 8, or at days 7, 9, and 11, showing that administration of anti-gp39 after induction of the disease significantly prevents EAE.

The results, which are presented in FIG. 2, indicate that administration of the first dose of anti-gp39 antibodies as late as 7 days after injection into the mice of PLP-peptide results in more than 60% suppression of the disease. Thus, anti-gp39 antibodies are capable of reversing or suppressing EAE.

The results further indicate that even though administration of a first dose of antibody only 7 days after induction of the disease in mice results in significant suppression of development of the disease, anti-gp39 treatment is somewhat more efficient when the first dose of antibody is administered sooner after induction of the disease.

Thus, administration of anti-gp39 antibodies to mice protects these mice from developing EAE upon induction of the disease and suppresses the disease in mice having EAE.

EXAMPLE 3

Suppression of EAE after spleen cell transfer of gp39 treated mice

Regulatory suppressor T-cells have been detected in Lewis rat, which have been recovered from EAE (Pesoa et al., *J. Neuroimmunol* 7:131, 1984) and after oral administration of myelin components (Lider et al.,*J. Immunol.* 142:748, 1989; Hafler et al., *Ann. NY Acad. Sci.* 636:251, 1991). It was postulated by Karpus and Swanborg (*J. Immunol.* 143:3492, 1989) that CD4$^+$ suppressor T-cells isolated from rats which have recovered from EAE, can down regulate EAE T-effector cells by differential inhibition of lymphokine production. In contrast, suppression of EAE in Lewis rats by oral administration of MBP is mediated by CD8$^+$ T-cells (Miller et al., *J. Exp. Med.* 174:791, 1991). To determine whether T cells of mice having been protected from EAE by administration of anti-gp39 antibody, are capable of protecting naive animals from EAE, the following example was undertaken.

In this example, a first set of mice were injected with 150 μg of PLP-peptide and a second set of mice were injected with 150 μg of PLP-peptide and anti-gp39 antibody according to the protocol described in Example 1. Four months later the mice were sacrificed by $CO_2$ euthanasia and the spleens were removed. Erythrocytes were removed by standard ammoniumchloride treatment (Mishell and Shiigi, *Selected Methods in Cellular Immunology*, W. H. Freeman and Company, 1980). Cells of individual spleens (500 μl) were injected i.v. in naive 5 Gy irradiated recipient female SLJ/j mice (10–12 weeks old). Two days after cell transfer, mice were challenged by intraperitoneal injection with 150 μg PLP-peptide following the procedure described in Example 1 and DAS scores determined.

Figure 3:
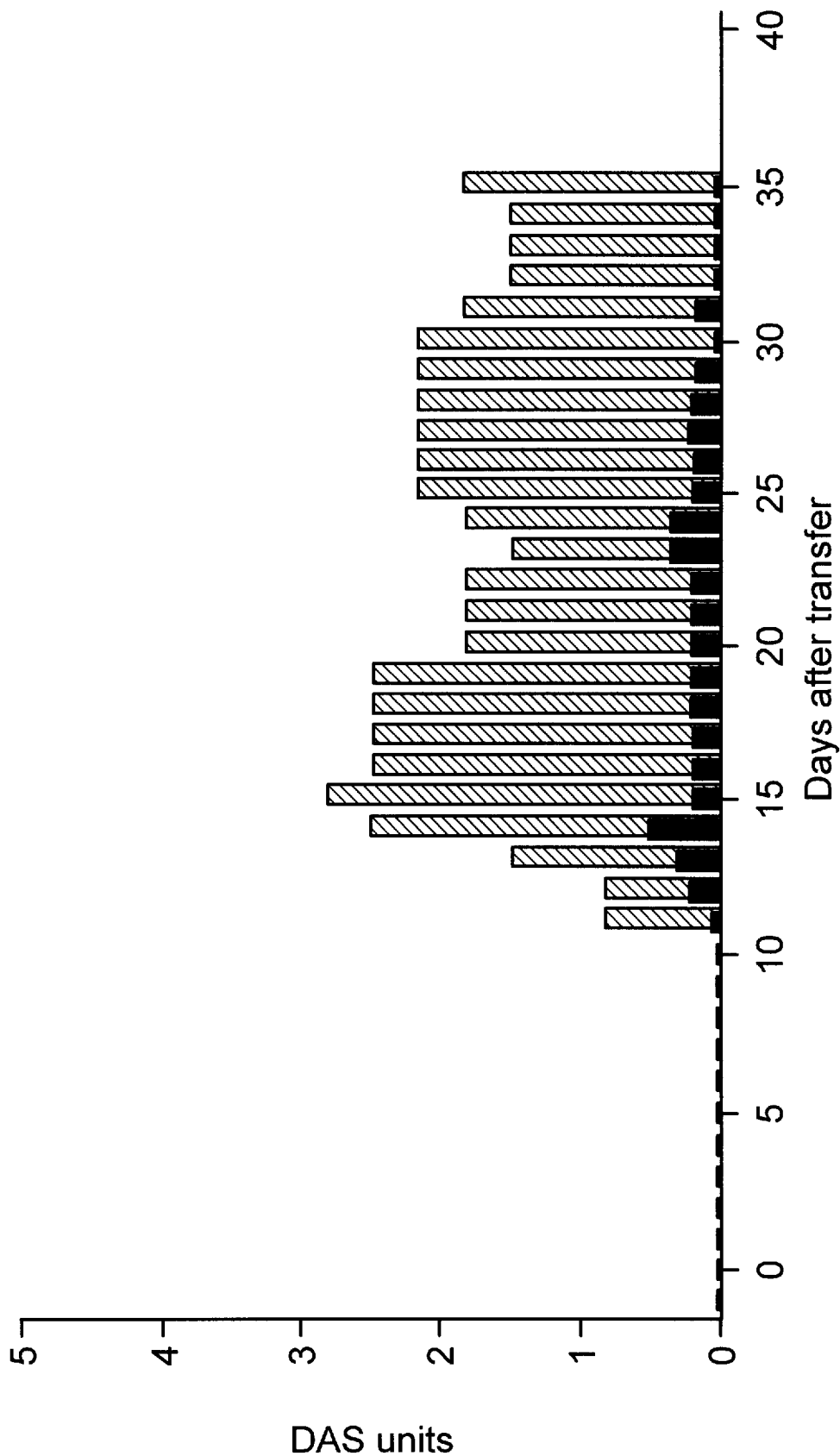
FIG. 3 is a graphical representation of DAS units measured daily in mice transplanted with donor spleen cells from mice injected with PLP-peptide and anti-gp39 antibodies (black bars) or with donor cells from mice injected with PLP-peptide alone (grey bars) and injected with PLP-peptide.

FIG. 3 represents the DAS scores of the animals. The results demonstrate that mice that have been transplanted with spleen cells from animals initially injected with PLP-peptide and anti-gp39 antibodies are protected from development of the disease, whereas mice transplanted with spleen cells from animals initially injected with PLP-peptide only develop EAE. Moreover, considering that the estimated half-life of antibodies is 12 days, it may be expected that no antibodies were present in the spleen cells transplanted in the mice. Therefore, the protective effect conferred by donor spleen cells from animals having received PLP-peptide and anti-gp39 antibodies cannot be explained by the presence of anti-gp39 antibodies. DAS scores of these mice indicates that suppression of EAE in the recipient mice is most likely due to the presence of a T-suppressor cell population in the transferred spleen cell suspension and that this T-suppressor cell population overrules the T-effector cell population efficiently.

EXAMPLE 4

Detection of gp39 positive Th-cells

This example demonstrates the presence of gp39 positive cells in the central nervous system of human subjects having multiple sclerosis.

Human autopsy central nervous system (CNS) tissues were obtained from the Netherlands brain bank, Amsterdam, the Netherlands. Gp39 positive cells were detected with an CD40-Ig fusion protein according to methods known in the art. CNS tissue sections of an MS patient and an Alzheimer patient were stained with CD40-Ig. In this example, only CNS tissues of MS-patients in which anti-MBP antibody forming cells were detected previously were used. The results of the staining show the presence of gp39 positive cells in a 8 μm coronal cerebrum section of an MS patient, but no gp39 positive cells were detected in coronal cerebrum sections of Alzheimer patients. Thus, gp39 positive cells were detected only in CNS tissue sections of MS patients. The presence of gp39 positive cells in MS-patient CNS tissue together with the detection of anti-MBP antibody forming cells in CNS tissues of MS-patients only and not in control CNS tissues indicates that such cells play an role in the pathological affected CNS tissues of MS patients.

In this study we have shown that suppression of B-cell activation by the administration of anti-gp39 Mabs, can result in the complete prevention of EAE development, dependent on the dose of antigen by which EAE was induced and dependent on the time period between EAE induction and administration of anti-gp39 Mabs. Although the exact mechanisms responsible for EAE induction and development are not clear, these data indicate that anti-gp39 antibody can be used for treatment of autoimmune diseases.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method of treating multiple sclerosis in a human subject in need of such treatment, comprising administering a therapeutically effective amount of an anti-human gp39 antibody.

2. The method of claim 1, wherein said antibody is a chimeric or humanized monoclonal antibody wherein said chimeric antibody comprises a non-human animal variable region and a human constant region.

* * * * *